(12) United States Patent
Draeger et al.

(10) Patent No.: US 6,175,035 B1
(45) Date of Patent: Jan. 16, 2001

(54) METHOD OF PRODUCING BETULINIC ACID

(75) Inventors: Birgit Draeger, Fichtestrasse 5, D-06114 Halle; Tino Galgon, Halle; Reinhard Neubert, Halle; Wolfgang Wohlrab, Halle, all of (DE)

(73) Assignee: Birgit Draeger, Halle (DE)

( * ) Notice: Under 35 U.S.C. 154(b), the term of this patent shall be extended for 0 days.

(21) Appl. No.: 09/310,163

(22) Filed: May 10, 1999

(51) Int. Cl.[7] .......................... C07C 61/29; A01N 65/00; A01N 45/00
(52) U.S. Cl. ....................... 560/116; 424/195.1; 514/169; 552/502
(58) Field of Search ........................ 424/195.1; 514/169; 552/502; 560/116, 117

(56) References Cited

U.S. PATENT DOCUMENTS

| | | | |
|---|---|---|---|
| 4,072,570 | * | 2/1978 | Williams ................................ 435/34 |
| 5,658,947 | * | 8/1997 | Dasgupta et al. ..................... 514/510 |
| 5,750,578 | * | 5/1998 | Carlson et al. ....................... 514/766 |
| 5,804,575 | * | 9/1998 | Pezzuto et al. ....................... 514/169 |
| 6,048,847 | * | 4/2000 | Ramadoss et al. ................... 514/169 |

* cited by examiner

Primary Examiner—Herbert J. Lilling
(74) Attorney, Agent, or Firm—Karl Hormann

(57) ABSTRACT

A method of producing betulinic acid from the bark of plane trees by fractional extraction with a solvent of medium polarity and subsequent recrystallization out of methanol.

12 Claims, No Drawings

METHOD OF PRODUCING BETULINIC ACID

BACKGROUND OF THE INVENTION

1. Field of the Invention

The invention, in general, relates to the production of betulinic acid and, more particularly, to a novel method of producing betulinic acid from plant fibers.

2. The Prior Art

Betulinic acid otherwise known as 3b-hydroxy-lup-20 (29)-en-28-acid ($C_{30}H_{48}O_3$) is a natural substance with a triterpene molecular structure and has been found in many plants. A specific effect of betulinic acid against the growth of cancer cells was described in 1995 by Pisha et al. in Nature Medicine 1, pp. 1046 seq. Amides of betulinic acid have been described as anti-HIV-agents with a new kind of effective mechanism in 1996 by Evers et al. in J. Med. Chem. 39, pp. 1056 seq. and by Soler et al. in J. Med. Chem. 39, pp. 1069 seq. This has led to a substantial increase in the demand for betulinic acid.

Methods of its production, for instance from the bark of *picramnia pentandra* (*simaroubaceae*) have been described by Herz et al. in Photochemistry, Vol. 11, 1972, pp. 3061 seq., and, from the bark of *arbutus menziesii* (*ericaceae*), by Robinson et al. in Photochemistry, Vol. 9, 1970, pp. 907 seq., and, from the bark of *ziziphus Mauritania* (*rhamnaceae*), by Pisha et al. In Nature Medicine, Vol. 1, pp. 1046 seq.

These starter materials are difficult to obtain, however. They require complex isolation processes, as the betulinic acid can be extracted only in admixture with other substances and it constitutes but a small proportion of the total abstract. Its separation requires multiple-stage cleaning by complex procedures, usually chromatographically. Thus, such production of betulinic acid is correspondingly expensive.

OBJECT OF THE INVENTION

It is an object of the invention to produce betulinic acid from readily available plant materials.

Another object of the invention resides in a method of producing betulinic acid from a plant material having a high betulinic acid content.

Moreover, it is an object of the invention to produce betulinic acid by a simple process.

BRIEF SUMMARY OF THE INVENTION

In accordance with the invention betulinic acid is produced by extraction from the bark of plane trees (sycamores) with solvents of medium polarity such as, for instance, dichloromethane, chloroform or diethylether, inspissation and recrystallization, preferably from methanol. While the bark of plane trees of the species *platanus acerifolia* is the currently preferred source, the bark of other species of the genus platanus may be equally useful for practicing the instant invention. In the event, extracts obtained with dichloromethane are contaminated by only a few accompanying substances. The advantage derived from the invention is that the bark of plane trees is easily obtainable. The trees are peculiar in that during the fall or autumn season the bark separates from, and is shed by, the trees so that it need only be collected. Unlike the gathering of the bark of other trees, there is no need for felling plane trees. A tree of a height of about 10 m supplies several kilograms of bark annually.

Moreover, because of the favorable component mixture of plane tree bark and the selected solvents, the process in accordance with the invention yields a pure product in a few stages without chromatography. The solvents may be recovered. This renders the process ecologically sound, quick and cost efficient. The process may be practiced with simple apparatus and on any scale.

In accordance with a further advantageous embodiment of the invention the betulinic acid can even from the first fractions of extraction be obtained with but insignificant contamination, by inspissation to about one fifth of its volume, recovering of the extraction medium. Double or treble recrystallization leads to a pure uncolored product. In another advantageous embodiment of the invention, further fractions of extraction are inspissated to a completely dry state and need be recrystallized only once.

Additional betulinic acid is obtained by adding hydrochloric acid to the methanolic original solution.

DETAILED DESCRIPTION OF THE PREFERRED EMBODIMENT

The invention will hereafter be described in greater detail with reference to an embodiment.

Plane tree bark which on its own separates from the tree is already in a relatively dry condition. The bark from that side of the trees which is not exposed to rain and which is not covered by algae is best suited as the starter material for clean extractions. After brief post drying (2–8 days) at room temperature the bark can easily be pulverized. To this end, the bark is first broken into smaller pieces and then ground in a breaker mill.

About 150 g of dried powder are extracted with dichloromethane by hydrostatic pressure in a glass tube. About seven fractions are obtained from one liter. Extraction is terminated once the reaction according to Liebermann-Burchardt is no longer positive, i.e. when violet coloring occurs no longer.

Fractions 1–4 are each inspissated to about 200 ml with the solvent being recovered. After several hours at −22° C. betulinic acid precipitates as a voluminous sediment of yellow color. From fractions 5 to 7 betulinic acid can be derived as a powder of slightly yellowish color by inspissation to a dry state.

All fractions of the extract are recrystallized out of methanol. To dissolve the sediment the methanol is heated to its boiling point and is then slowly cooled to 4° C. Sediments from fractions 1 to 4 require 2 to 3 recrystallizations until the original solution is also colorless. The sediments of fractions 5 to 7 require recrystallization only once.

Even after the first recrystallization the betulinic acid from any of the fraction is chromatographically pure (thin-layer chromatography; gas chromatography; see infra) even though some of it may be still colored yellow. The methanol can be recovered by distillation which renders this stage of the process ecologically sound while saving resources.

The yield during crystallization can be increased by the addition of a few drops of hydrochloric acid to the original solution after separation of the first crop of crystals and by leaving it untended at 4° C. for several hours.

The identity of the betulinic acid obtained in the manner described supra is established by a thin-layer chromatographic analysis and gas chromatographic analysis as well as by mass spectrometry and $^1$H-NMR.

What is claimed is:

1. A method of producing betulinic acid comprising the steps of:

gathering bark from plane trees;

drying the bark;

grinding the bark to a powder;

subjecting the powder to fractional extraction with a solvent of medium polarity by hydrostatic pressure in a glass tube; and terminating the extractions when the Liebermann-Burchardt reaction is no longer positive.

2. The method of claim 1, wherein the bark is gathered from the side of plane trees subjected to less rain.

3. The method of claim 1, wherein the solvent is dichloromethane.

4. The method of claim 3, further comprising the steps of inspissating initial fractions to about one fifth of their volume.

5. The method of claim 4, further comprising the step of cooling the inspissated fractions to −22° C. to precipitate the betulinic acid as a voluminous sediment.

6. The method of claim 5, further comprising the step of recrystallizing each fraction at least once out of methanol.

7. The method of claim 6, wherein the sediment is dissolved by heating the methanol to its boiling point followed by slow cooling to 4° C.

8. The method of claim 7, further including the step of chromatographically establishing the purity of the betulinic acid.

9. The method of claim 3, further including the step of inspissating terminal fractions to their dry state.

10. The method of claim 9, further comprising the step of recrystallizing the dried fractions out of methanol at least once.

11. The method of claim 10, wherein the dried fractions are dissolved in methanol by heating it to its boiling point and subsequently slowly cooled to 4° C.

12. The method of claim 11, further including the step of chromatographically establishing the purity of the betulinic acid.

* * * * *